United States Patent [19]

Dorlars et al.

[11] B 3,994,834

[45] Nov. 30, 1976

[54] TRIAZOLYL STILBENE BRIGHTENERS METHOD OF PREPARING AND DETERGENTS THEREWITH

[75] Inventors: Alfons Dorlars, Leverkusen; Heinrich Gold, Bergisch-Gladbach; Walter Horstmann, Bergisch-Gladbach, Schildgen, all of Germany

[73] Assignee: Bayer Aktiengesellschaft, Leverkusen, Germany

[22] Filed: Oct. 5, 1973

[21] Appl. No.: 403,766

[44] Published under the second Trial Voluntary Protest Program on February 10, 1976 as document No. B 403,766.

[30] Foreign Application Priority Data

Oct. 5, 1972    Germany............................ 2248820

[52] U.S. Cl................................ 252/543; 252/524; 260/240 C
[51] Int. Cl.².................. C07D 249/20; C11D 3/28
[58] Field of Search.................. 260/240 C; 252/543

[56] References Cited
UNITED STATES PATENTS

| | | | |
|---|---|---|---|
| 2,927,866 | 3/1960 | Williams et al. | 260/240 C X |
| 3,453,268 | 7/1969 | Dorlars et al. | 260/240 C |
| 3,485,831 | 12/1969 | Dorlars et al. | 260/240 C |
| 3,578,653 | 5/1971 | Wallace | 260/240 C X |

*Primary Examiner*—Allen B. Curtis
*Attorney, Agent, or Firm*—Plumley and Tyner

[57] ABSTRACT

The stilbene compound of the formula

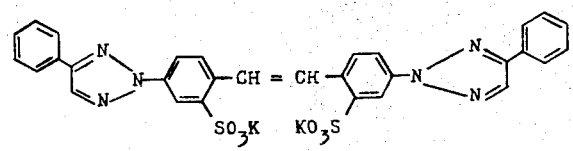

exists in three crystal modifications. Two of them are valuable as brighteners for preparing colorless detergents. The stilbene compound is prepared from the corresponding sulphonic acids, their mono- or disodium salts.

7 Claims, No Drawings

TRIAZOLYL STILBENE BRIGHTENERS METHOD OF PREPARING AND DETERGENTS THEREWITH

The present invention relates to the stilbene compound of the formula

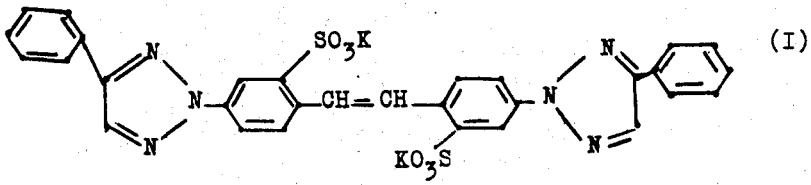

especially three crystal modifications of this compound, processes for its manufacture, and its use as a brightener for detergents.

German Pat. Spec. No. 1,279,636 has already described the free sulphonic acid and the disodium salt of the compound of the formula (I). The free disulphonic acid and the disodium salt suffer from the disadvantage that when incorporated into white detergents they discolour the detergents green. This discolouration narrows the industrial importance of the detergents and hence of the brightener considerably.

It has now been found, surprisingly, that these difficulties can be avoided by using the dipotassium salt, especially of the β- and γ-modification.

The dipotassium salt exists in 3 modifications which are characterised by X-ray diffraction spectra. These are one green, needle-shaped modification, the so-called α-form, and two yellowish-white modifications, the β- and γ-forms.

The potassium salt of the formula (I) is manufactured by reaction of the free disulphonic acid or of its acid sodium salt of the disodium salt, in an aqueous medium, with preferably at least equimolar amounts of water-soluble potassium salts or potassium compounds, especially potassium hydroxide, potassium carbonate, potassium chloride or potassium sulphate, at temperatures between 20° and 150°C, optionally under pressure and optionally in the presence of organic water-miscible solvents such as alcohols, ketones or esters or mixtures of such solvents.

Examples of alcohols which can be used are methanol, ethanol and isobutanol, examples of ketones which can be used are acetone and methyl ethyl ketone and examples of esters which can be used are acetic acid ethyl ester and acetic acid butyl ester.

In a preferred embodiment, the disodium salt is stirred, in water, with at least equivalent amounts of potassium carbonate and/or potassium chloride for 5 minutes to 4 hours at a temperature of about 90°C to 120°C. This produces the crystals of the γ-modification at about 100°C whilst at about 115°C the crystals of the β-modification are formed. The crystals of the β-modification are distinguished by a particularly coarse habit, which is recognisable even from the fact that the crystals separated from the mother liquor only retain about 15 to 35% of mother liquor, which produces an additional purification effect.

The three modifications of the potassium salt are used as optical brighteners for detergents. The β- and γ-form are distinguished in that, in contrast to the α-form, they do not produce, on incorporation into a washing powder of customary composition, a green discolouration which becomes particularly visible on moistening the washing powder. The same green discolourations are obtained on using the free disulphonic acid of the compound of the formula (I) or its disodium salt.

The advantage of the preferred process is that this crystal form which does not discolour the washing powder is obtained direct from the disodium salt, either from already existing powders and pastes which have been isolated, or on precipitation of the disodium salt from the aqueous solution produced after the purification.

The manufacture of the α-form of the compound (I) is effected by neutralising the free disulphonic acid of the compound (I) with potassium hydroxide solution or potassium carbonate in aqueous solution or suspension at temperatures between 20° and 110°C. The α-modification is thereby obtained in the form of light green needle-shaped crystals.

The evaluation of the X-ray diffraction diagram of the α-form by means of the Bragg equation gives the following d-values. The corresponding intensities are estimated.

| d-Values, Å | Intensity |
|---|---|
| 16.86 | 100 |
| 12.39 | 30 |
| 5.79 | 60 |
| 3.78 | 40 |

Heating the α-form of the compound (I), in aqueous potassium carbonate solution, to temperatures of 50 to 150°C, if appropriate under pressures of up to 10 atmospheres gauge, gives the crystalline, yellowish white β-form. Since the β-form is obtained in relatively large crystals of up to 1 mm length, it proved possible to characterise the substance by a single-crystal X-ray investigation. This showed a monoclinic symmetry. The space group is $P^{2_1}/b$ (according to Hermann-Mauguin) or $C_{2h}^5$ (according to Schönfliess). The monoclinic angle α is 80.714° ± 0.003°, the cell volume is 3,146.8 ± 0.3 Å$^3$ and the length of the ortho-axis $a = 9.6381 \pm 0.0004$ Å.

In a powder photograph of the β-form, the following d-values and intensities were measured.

| d-Values [Å] | Intensities (estimated) |
|---|---|
| 20.20 | 100 |
| 3.99 | 50 |
| 3.69 | 50 |
| 2.91 | 30 |

The β-form can also, as already described, advantageously be obtained direct from the disodium salt.

In addition to the α- and β-form of the compound of the formula (I) there also exists a γ-form which is obtained, for example, by heating the α-form, in aqueous alcohols, to temperatures of 50° to 120°C. The γ-form consists of fine needle-shaped yellowish white crystals which generally are 20 to 50μ long. The X-ray investigation of the γ-form gave the following d-values and intensities.

| d-Values, A | Intensities (estimated) |
|---|---|
| 19.97 | 100 |
| 6.45 | 40 |
| 4.89 | 30 |
| 3.60 | 80 |

In practice, the β- and γ-form of the compound of the formula (I) are employed as brighteners for washing powders and these forms give a very good white shade of textile material, especially of cellulose and synthetic polyamides. The β- and γ-form are incorporated in the form of powders which are obtained by grinding with, for example, potassium carbonate, or fine granules, which are obtained by spray drying, into the washing powders.

EXAMPLE 1

62.6 g of 4,4'-bis-[4-phenyl-v-triazolyl-(2)]-stilbene-2,2'-disulphonic acid containing 30% of disodium salt are suspended in 500 g of water and neutralised with a solution of 5.6 g of potassium hydroxide in 50 ml of water. The mixture is stirred for 2 hours at 60°C. Whilst doing so, the pH value is adjusted to 7–8 by addition of further dilute potassium hydroxide solution if required. The product is filtered off at room temperature, rinsed with 100 ml of water used in portions and dried to constant weight at 50°C in a vacuum cabinet. 68 g of the α-form of the compound of the formula (I) are obtained.

EXAMPLE 2

62.6 g of 4,4'bis-[4-phenyl-v-triazolyl-(2)]-stilbene-2,2'-disulphonic acid are neutralised as described in Example 1, 10 g of potassium hydroxide are added to the suspension of the potassium salt and the mixture is then heated to 120°C in an autoclave for 4 hours. The crystals formed are filtered off at 40°C, washed with 100 ml of a 1% strength potassium carbonate solution and dried to constant weight in a vacuum cabinet at 50°C. 65 g of the β-form of the compound of the formula (I) are obtained.

EXAMPLE 3

70.2 g of α-modification are dissolved in 2,600 ml of water at 95° to 98°C to give a clear solution and the latter is adjusted to pH 10 with a little potassium hydroxide solution. The resulting solution is cooled to 20° – 25°C over the course of 2 hours. The product which has precipitated is filtered off, washed with 500 ml of water and dried in vacuo at 50°C. 63 g of the γ-modification of the potassium salt of the formula (I) are obtained.

EXAMPLE 4

22 g of disodium 4,4'-bis-(4-phenyl-v-triazolyl-2)-stilbene-2,2'-disulphonate are stirred into 300 ml of water and the suspension is kept for 10 minutes at 90°C. 10 g of potassium carbonate are now added and the reaction mixture is kept for 4 hours in a closed vessel at a temperature of 115°C. After this time, the mixture is cooled and the crystals which have precipitated are filtered off and washed with 100 ml of 5% strength potassium carbonate solution. 26.5 g of a moist crystal mass containing 18% of mother liquor are obtained; after drying, 22.5 g of an only pale yellowish-coloured crystal powder of the β-modification of the potassium salt of the formula (I) remain.

EXAMPLE 5

129.5 g of an aqueous paste containing 22% of disodium 4,4'-bis-(4-phenyl-v-triazolyl-2)-stilbene-2,2'-disulphonate are stirred with 325 ml of water. 13 g of potassium carbonate are added at 90°C and the mixture is kept for 4 hours in a closed vessel at 115°C. After cooling, filtration and washing with 5% strength potassium carbonate solution, 42 g of a moist crystal mass containing 33% of mother liquor are obtained; after drying, 28 g of a crystal powder of the β-modification of the potassium salt of the formula I, which has only a pale yellowish-greenish colour, remain.

EXAMPLE 6

350 ml of a solution, obtained according to the customary purification methods, containing 11 g of disodium 4,4'-bis-(4-phenyl-v-triazolyl-2)-stilbene-2,2'-disulphonate, are treated dropwise, at 100°C, with a solution of 5 g of potassium carbonate in 10 ml of water. After 1 hour at 100°C a further 5 g of potassium chloride are added and after a further hour at 100°C the suspension is cooled to room temperature. It is filtered and the crystals are washed with 50 ml of 5% strength potassium carbonate solution. Yield 16.4 g of moist crystals, representing 11.5 g of dipotassium 4,4'-bis-(4-phenyl-v-triazolyl-2)-stilbene-2,2'-disulphonate in the form of a pale yellowish crystal powder of the γ-modification.

EXAMPLE 7

A solution of 10 g (approx. 15 mmols) of the disodium salt of 4,4'-bis-[4-phenyl-v-triazolyl-(2)]-stilbene-2,2'-disulphonic acid in 300 ml of water is treated with 4.5 g (60 mmols) of potassium chloride at 95°C, whilst stirring. The mixture is stirred for a further 5 minutes at 95° to 100°C and the yellowish-tinged white dipotassium salt which immediately precipitates as crystals is allowed to settle out whilst cooling and is filtered off at approx. 30°C and dried. 10 g of yellowish-tinged white dipotassium salt are obtained.

EXAMPLE 8

To manufacture a detergent, 2.5 g of carboxymethylcellulose are first allowed to swell in 40 ml of cold water, 40 g of 50% strength dodecylbenzenesulphonate, 65 g of sodium tripolyphosphate and 15 g of waterglass (65% strength) are then added whilst stirring and a suspension of 200 mg of the γ-modification of the compound of the formula (I) in 10 ml of water is introduced. The mixture is stirred for 5 minutes at 50°C, dried on a twin roll drier at 130°C and sieved using a sieve of 2 mm mesh width. Approx. 110 g of a white washing powder are obtained.

If instead of the γ-form the β-form is employed, a detergent with excellent properties is again obtained. On moistening the washing powders with water, no discolouration occurs.

The needle-shaped green α-modification gives a green washing powder, similarly to the disodium salt and to the free disulphonic acid of the compound of the formula (I).

We claim:
1. The compound of the formula

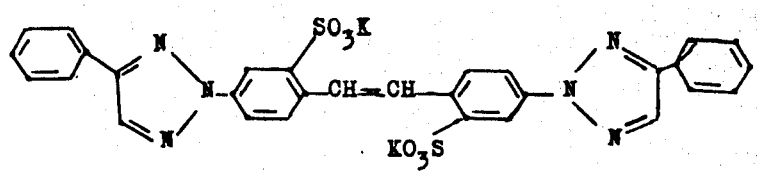

in the β-modification, characterised by the following d-values in the X-ray spectrum: 20.20 A; 3.99 A; 3.69 A and 2.91 A.

2. Detergents brightened with compounds of claim 1.
3. The compound of the formula

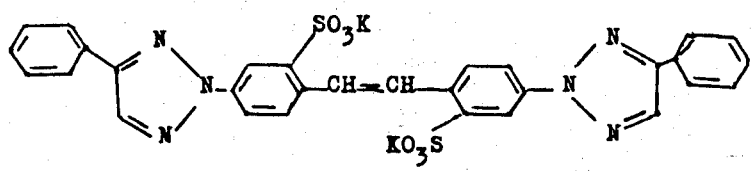

in the γ-modification, characterized by the following d-values in the X-ray spectrum; 19.97 A; 6.45 A; 4.89 A; and 3.60 A.

4. Detergent brightened with the compound of claim 3.

5. Process for the manufacture of the compound of the formula (I)

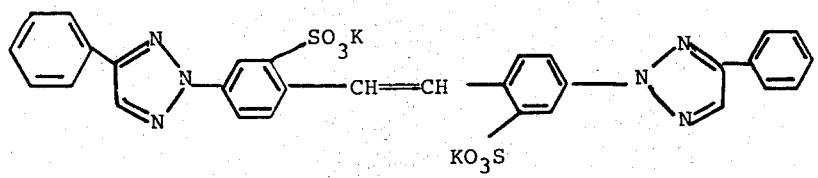

characterised in that the disodium salt thereof is reacted in water at a temperature of 90°–120° C with potassium carbonate and/or potassium chloride.

6. Process according to claim 5, characterised in that it is carried out under pressures of up to 10 atmospheres gauge.

7. Process according to claim 5, characterised in that the reaction is carried out in the presence of alcohols, ketones or esters.

* * * * *